United States Patent
Hansson et al.

(10) Patent No.: US 11,293,882 B2
(45) Date of Patent: Apr. 5, 2022

(54) SAMPLE HOLDER

(71) Applicant: OREXPLORE AB, Kista (SE)

(72) Inventors: Alexander Hansson, Kista (SE); Mikael Bergqvist, Kista (SE)

(73) Assignee: OREXPLORE AB, Kista (SE)

( * ) Notice: Subject to any disclaimer, the term of this patent is extended or adjusted under 35 U.S.C. 154(b) by 91 days.

(21) Appl. No.: 16/483,926

(22) PCT Filed: Feb. 5, 2018

(86) PCT No.: PCT/EP2018/052820
§ 371 (c)(1),
(2) Date: Aug. 6, 2019

(87) PCT Pub. No.: WO2018/141967
PCT Pub. Date: Aug. 9, 2018

(65) Prior Publication Data
US 2020/0096460 A1  Mar. 26, 2020

(30) Foreign Application Priority Data

Feb. 6, 2017  (SE) .................................... 1750098-4

(51) Int. Cl.
*G01N 23/20025*  (2018.01)
*G01N 23/2204*  (2018.01)
(Continued)

(52) U.S. Cl.
CPC ..... *G01N 23/20025* (2013.01); *G01N 23/223* (2013.01); *G01N 23/2204* (2013.01);
(Continued)

(58) Field of Classification Search
CPC ......... G01N 23/20025; G01N 23/2204; G01N 23/223; G01N 33/24; G01N 2223/03; G01N 2223/076; G01N 2223/307
See application file for complete search history.

(56) References Cited

U.S. PATENT DOCUMENTS 2,260,562 A * 10/1941 Dillon .................. E21B 47/026
324/377
3,855,470 A * 12/1974 Sahores ................. G01N 23/20
378/73
(Continued)

FOREIGN PATENT DOCUMENTS

CN     205628041 U    10/2016
EP     2 085 772 A1   8/2009

OTHER PUBLICATIONS

International Search Report and Written Opinion dated Apr. 17, 2018, issued in corresponding International Application No. PCT/SE2018/052820, filed Feb. 5, 2018, 13 pages.

*Primary Examiner* — Blake C Riddick
(74) *Attorney, Agent, or Firm* — Christensen O'Connor Johnson Kindness PLLC

(57) ABSTRACT

A sample holder for holding a sample comprising a drill core sample or drill cuttings during X-ray transmission measurements and fluorescence measurements is disclosed. The sample holder comprises a confining structure having an axial direction and being adapted to, during measurement, at least partially enclose the sample and to restrict movement of the sample in a direction intersecting the axial direction. The confining structure comprises at least one region facing away from the axial direction and allowing exciting radiation impinging on, and fluorescent radiation emanating from, the sample during measurement to pass therethrough. An apparatus adapted for receiving such a sample holder is also disclosed, comprising a ray source, an X-ray transmission detector, a fluorescence detector and rotating means for rotating at least one of the sample holder, the X-ray source, the X-ray transmission detector and the fluorescence detector. Further, a system comprising such a sample holder and apparatus is disclosed.

15 Claims, 3 Drawing Sheets

(51) Int. Cl.
*G01N 23/223* (2006.01)
*G01N 33/24* (2006.01)

(52) U.S. Cl.
CPC ......... *G01N 33/24* (2013.01); *G01N 2223/03* (2013.01); *G01N 2223/076* (2013.01); *G01N 2223/307* (2013.01)

(56) References Cited

U.S. PATENT DOCUMENTS

| | | | | |
|---|---|---|---|---|
| 4,224,517 | A | | 9/1980 | Lubecki et al. |
| 4,575,869 | A | * | 3/1986 | Torrisi ................. G01N 23/083 378/47 |
| 4,821,303 | A | * | 4/1989 | Fawcett ............... G01N 23/207 378/71 |
| 5,781,608 | A | * | 7/1998 | Tomie .................... H05G 2/001 378/119 |
| 5,866,907 | A | * | 2/1999 | Drukier ................. G01N 33/60 250/328 |
| 7,436,926 | B2 | | 10/2008 | Matoba et al. |
| 2002/0172322 | A1 | * | 11/2002 | Kawahara ............ G01N 23/223 378/45 |
| 2002/0176536 | A1 | * | 11/2002 | Ayukawa ............. G01N 23/223 378/66 |
| 2005/0232393 | A1 | * | 10/2005 | Moriyama ........... G01N 23/223 378/47 |
| 2007/0211852 | A1 | | 9/2007 | Matoba |
| 2011/0044426 | A1 | * | 2/2011 | Ullberg ................ G01N 23/223 378/45 |
| 2011/0317813 | A1 | * | 12/2011 | Matsushita ............. H01J 35/10 378/73 |
| 2014/0072095 | A1 | | 3/2014 | Feser et al. |
| 2014/0146940 | A1 | * | 5/2014 | Zarkadas ............... G01N 23/22 378/44 |
| 2017/0052128 | A1 | * | 2/2017 | Yun ...................... G01N 23/223 |

\* cited by examiner

SAMPLE HOLDER

TECHNICAL FIELD

The present disclosure generally relates to the field of analysis of drill core samples and/or drill cuttings. In particular, the present disclosure relates to a sample holder for holding a sample during X-ray transmission measurements and fluorescence measurements.

BACKGROUND

In mineral exploration, gathering accurate information about known or potential ore deposits may be important for geologists in order to assess whether to begin, continue or abandon mining operations within a certain area. Using specialized drills, samples of rock may be withdrawn from an orebody in the form of drill cores and/or drill cuttings, and analyzed for e.g. mineral contents, stratigraphic data and/or other geological information that may be of importance to the geologist.

To analyze the drill core samples and/or drill cuttings, various flavors of measurements may be performed in order to gather data about the samples before attempting to analyze and identify the constituents of for example the rock from where the samples were withdrawn. Using X-ray transmission measurements (e.g. for tomography), one or more two-dimensional slices revealing the interior of the sample may be obtained by measuring the differences in X-ray attenuation that arise from differences in e.g. density and composition within the sample. Volumetric data may be obtained by combining several such slices, and three-dimensional inspection of the interior of the sample may be performed.

Using fluorescence measurements, the concentrations of chemical elements in the sample may be determined by measuring the fluorescent (secondary) rays emitted from the sample when excited by a primary ray source. By knowledge of what elements would generate what fluorescent rays, the material composition of the sample may be studied. Information about the chemical composition of the sample may also be obtained by using X-ray transmission measurements and knowledge about so called absorption edges.

By combining several techniques, such as both X-ray transmission analysis and fluorescence analysis, a more complete knowledge about the site or deposit being examined may be deduced.

In order not to limit the accuracy or resolution of X-ray tomography or X-ray transmission analysis and for the fluorescence measurements to be representative, it may be important that the sample is held fixed during measurement, also in those cases where the drill core samples are broken into pieces. At the same time, it is desirable that the fixing of the sample does not negatively affect the intensity of the measurements.

In light of the above, there is a need for an improved sample holder suitable for both X-ray transmission and fluorescence measurements on drill core samples and/or drill cuttings.

SUMMARY

An objective of the present disclosure is therefore to at least partially fulfill the above requirements. This and other objectives are achieved by means of a sample holder for holding a sample during both X-ray transmission measurements and fluorescence measurements as defined in the independent claim. Further embodiments of the present disclosure are provided in the dependent claims.

According to one aspect, a sample holder for holding a sample during X-ray transmission measurements (e.g. for tomography) and fluorescence measurements is provided. The sample may include a drill core sample and/or drill cuttings. The sample holder may include a confining structure that has an axial direction and that is adapted to, during measurement, at least partially enclose the sample and to restrict movement of the sample in a direction that intersects the axial direction. The confining structure may include at least one region that faces away from the axial direction, and that allows exciting radiation that impinges on, and fluorescent radiation that emanates from, the sample during measurement to pass therethrough.

By restricting the sample from moving in a direction that intersects the axial direction, the sample may be held fixed such that it does not move in an unwanted direction or in an unwanted way during measurement. This may result in an improved resolution and a more accurate result, especially for X-ray transmission measurements but also for fluorescence measurements.

While the sample is held fixed, in the above sense, radiation coming from e.g. a ray source may pass through the at least one region that faces away from the axial direction and impinge on the sample, with little or no attenuation caused by the sample holder itself. Likewise, radiation emanating from the sample during e.g. fluorescence measurements may pass through the at least one region that faces away from the axial direction and reach e.g. a ray detector also with little or no attenuation caused by the sample holder itself. This may result in an improved resolution and a more accurate result, especially for fluorescence measurements but also for X-ray transmission measurements.

A sample holder in accordance with the present disclosure thereby achieves the synergetic effect of both fixing the sample during measurement, and at the same time allowing for radiation to impinge on, or emanate from, the sample with little or no attenuation due to the sample holder itself.

Herein, rays may for example be X-rays or ultraviolet (UV) rays, and the corresponding measurements may for example be X-ray transmission measurements, X-ray fluorescence (XRF) measurements and/or UV fluorescence measurements. Likewise, a ray source may be for example an X-ray source, and a ray detector may for example be an X-ray detector or a UV detector. By using X-rays, radiation having enough energy to penetrate deeper into and/or all the way through the sample may be possible. This may allow e.g. for tomographic measurements, and/or for fluorescence measurements of rays emanating from deeper within the sample than its outermost surface.

It is also envisaged that rays belonging to other parts of the electromagnetic spectrum may be used, if suitable, and that also different types of rays (such as e.g. both X-rays and UV rays) may be used in combination.

In one embodiment, the confining structure may be rigid. Having a rigid confining structure may further help to keep the sample fixed and steady during measurement. A rigid confining structure may for example have a Young's modulus of above or equal to 1.0.

In one embodiment, the confining structure may comprise a shape that conforms to a hollow cylinder. This may be beneficial especially when the sample is a drill core sample, as such samples are usually cylindrical in shape and may be positioned symmetrically in the sample holder within, and with respect to, the confining structure.

In one embodiment, the confining structure may be formed from a polymer material. The polymer material may for example be a plastic or similar.

In one embodiment, the polymer material may have a majority of atoms with atomic number 9 or less. Polymer materials having atoms with low atomic numbers may help to reduce the amount of radiation attenuated by the sample holder, especially during X-ray measurements.

In one embodiment, the at least one region may include a hole through the confining structure. A hole may offer the lowest possible attenuation of radiation impinging on or emanating from the sample.

In one embodiment, the at least one region may have a reduced finite thickness. A region with reduced finite thickness may offer low or no attenuation of radiation, while reducing e.g. the risk of samples in the form of e.g. drill cuttings or smaller pieces escaping from the confining structure through the region during measurement.

In one embodiment, the sample holder may be adapted such that, during measurement, the axial direction aligns with a direction of gravity. By aligning the axial direction with a direction of gravity, the sample may be further fixed by its own weight and kept from moving in an unwanted direction or in an unwanted way even if e.g. the confining structure has a width or another transversal dimension larger than that of the sample.

In one embodiment, the confining structure may include a plurality of regions facing away from the axial direction and allowing exciting radiation impinging on, and fluorescent radiation emanating from, the sample during measurement to pass therethrough. By having two or more such regions, low or no attenuation of radiation may be achieved in more than one directions.

In one embodiment, the regions in the plurality of regions may be arranged in an ordered pattern. The pattern may be optimized to maximize or at least improve the outcomes of certain measurement positions (i.e. relations between the sample, a ray source and a ray detector) in terms of e.g. accuracy and precision, or in terms of e.g. specific properties of the sample that are also arranged in an ordered pattern.

In one embodiment, the ordered pattern may be one of a rhombic, hexagonal, rectangular, square or parallelogrammic lattice, or an ordered but not periodic quasicrystalline pattern.

In one embodiment, the regions in the plurality of regions may be arranged in a random pattern. Arranging the regions in a random pattern may be beneficial if for example an average of some property is to be estimated for the sample, and/or in that a bias in measurements related to the position of regions may be circumvented.

In one embodiment, the at least one region may extend along a direction that forms an angle to a plane perpendicular to the axial direction.

In one embodiment, the angle to the plane perpendicular to the axial direction may be between 0 to 90°, preferably between 0 to 45°, and more preferably approximately 0°.

According to one embodiment, an apparatus for X-ray transmission measurement and fluorescence measurement of samples may be provided. The samples may include drill core samples and/or drill cuttings. The apparatus may be adapted to receive a sample holder as described above. The apparatus may include an irradiation or ray source, an X-ray transmission detector and a fluorescence detector. The apparatus may further include means for rotating at least one of the sample holder, the ray source, the X-ray transmission detector and the fluorescence detector. Preferably, if rotating the sample holder, the sample holder is rotated around its axial direction (i.e. around its length axis).

In one embodiment, the apparatus may be configured such that during rotation of at least one of the sample holder, the ray source and the fluorescence detector, a plane of an extension of the at least one region of the sample holder at least momentarily aligns with a plane defined by the positions of the ray source, the fluorescence detector and the at least one region of the sample holder. By aligning the plane of the extension of the at least one region with the plane, the time window for measurement of the sample through the at least one region may be longer, allowing e.g. more measurement data to be collected through the at least one region during rotation.

In one embodiment, the apparatus may be configured such that the plane of the extension of the at least one region of the sample holder aligns with the plane for at least one full rotation of at least one of the sample holder, the ray source and the fluorescence detector. By so doing, the time window available for measurement through the at least one region may be further extended.

In the context of the present disclosure, the axial direction of the confining structure is defined as the axis along which the confining structure extends. For example, if the confining structure is assumed (for illustrative purposes only) to be a cylinder of a length (L) and a diameter (D), where L>D, then the axial direction of the confining structure would be along the length of the cylinder. It is, of course, envisaged herein that the confining structure may have a shape other than that of a cylinder, but it may be assumed that the length of the confining structure would usually align with its axial direction.

In one embodiment, the ray source may be an X-ray source, and at least one of the fluorescence detectors may be an X-ray detector. Likewise, the fluorescence measurements may be X-ray fluorescence (XRF) measurements.

In one embodiment, a system for X-ray transmission measurement and fluorescence measurement of samples such as drill core samples or drill cuttings may be provided. The system may include a sample holder as described above and an apparatus as described above.

Herein, a fluorescence detector and an X-ray transmission detector may be of different types, each tailored for their respective purpose. It is also envisaged that a fluorescence detector and an X-ray transmission detector may be of a same type, and that the same type of detector serves different purposes depending e.g. on where it is positioned (i.e. to capture fluorescent rays or transmitted rays).

Herein, a region is defined as a region of the confining structure where the attenuation (or scattering) of ray radiation is less or absent compared to a part of the confining structure that surrounds the region. A region may for example be a hole in the confining structure, or a region of the confining structure with a reduced but finite thickness. A region may also be a region of the confining structure having a different material than a part of the confining structure that surrounds the region. Herein, the term region may be used interchangeably with one or more of the terms window or aperture, with regards to radiation, even though it may have a finite thickness. If X-ray radiation is used, the region may for example be transparent to or have little attenuation of X-rays while being opaque to or having high attenuation of e.g. visible light.

It will be appreciated that the confining structure may be formed of two or more different materials or structural elements. In one example, the confining structure may comprise a first material providing structural robustness or form stability, and a second material allowing the exciting radiation and/or fluorescent radiation to pass through the structure.

The present disclosure relates to all possible combinations of features recited in the claims and mentioned herein, including the ones listed above as well as other features which will be described in what follows with reference to different embodiments. Any embodiment described herein may be combinable with other embodiments also described herein, and the present disclosure relates to all such combinations.

Further objects and advantages of the various embodiments of the present disclosure will be described below by means of exemplifying embodiments.

BRIEF DESCRIPTION OF THE DRAWINGS

The above, as well as additional objects, features, advantages and applications of the inventive sample holder, will be better understood through the following illustrative and non-limiting detailed description of embodiments. Reference is made to the appended drawings, in which.

Figure 1A:
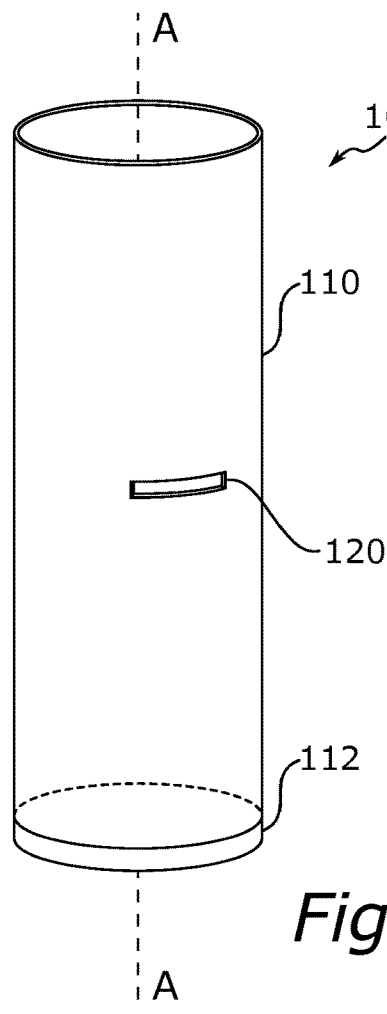
FIGS. 1a, 1b and 1c illustrate a sample holder according to one or more embodiments of the present disclosure.

In the drawings, like reference numerals will be used for like elements unless stated otherwise. Unless explicitly stated to the contrary, the drawings show only such elements that are necessary to illustrate the example embodiments, while other elements, in the interest of clarity, may be omitted or merely suggested. As illustrated in the figures, the sizes of elements and regions may be exaggerated for illustrative purposes and, thus, are provided to illustrate the general structures of the embodiments.

DETAILED DESCRIPTION

Exemplifying embodiments will now be described more fully hereinafter with reference to the accompanying drawings. The drawings show currently preferred embodiments, but the invention may, however, be embodied in many different forms and should not be construed as limited to the embodiments set forth herein; rather, these embodiments are provided for thoroughness and completeness, and fully convey the scope of the present disclosure to the skilled person.

Figure 1B:
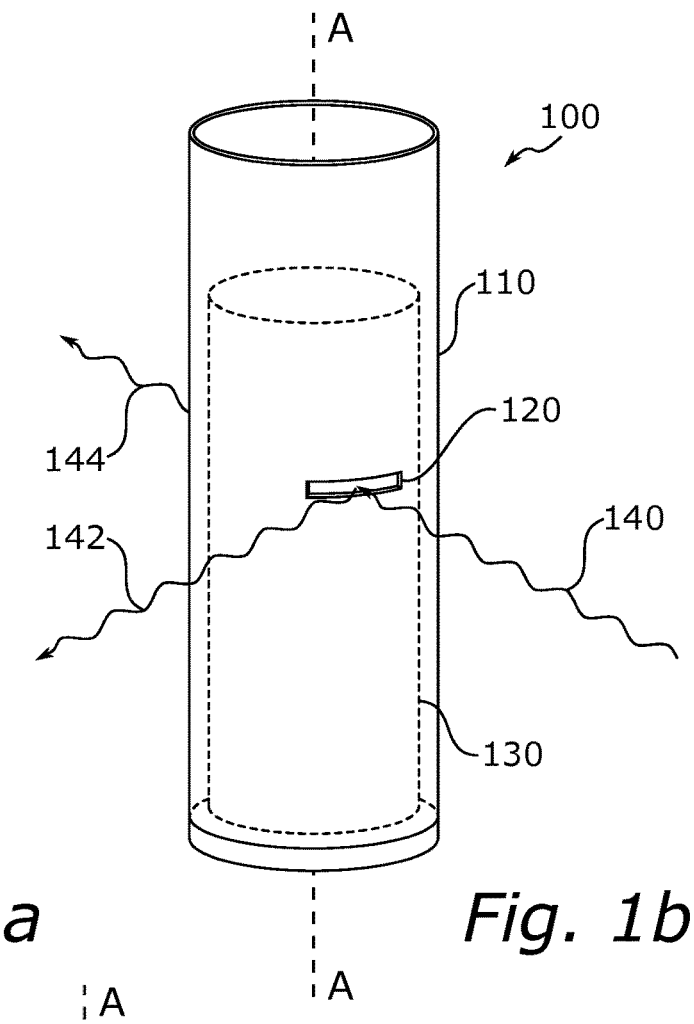
Figure 1C:
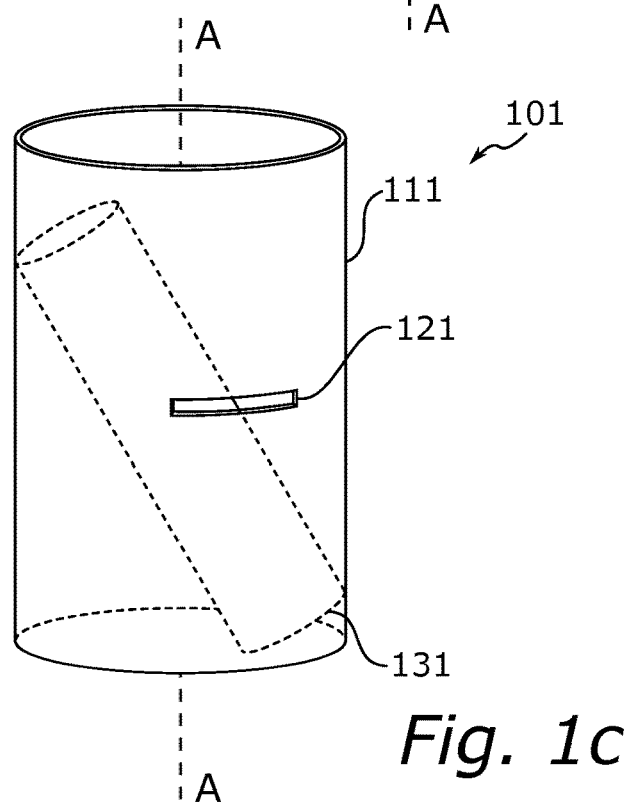

With reference to FIGS. 1a, 1b and 1c, a sample holder for holding a sample including a drill core sample or drill cuttings during X-ray transmission measurement and X-ray fluorescence measurement will be described in more detail. Although the illustrated examples described in what follows all relate to measurements involving X-rays, it is, as described earlier, also envisaged that other rays (such as UV rays) and suitable sources and/or detectors may be used, at least for fluorescence measurements.

FIG. 1a illustrates a sample holder 100. The sample holder 100 may include a confining structure 110 that has an axial direction A. Here, the confining structure 110 of the sample holder 100 is formed as a hollow cylinder. It is, however, envisaged that the confining structure 110 may have other forms, and be shaped as for example a square, rectangular, oval, hexagonal or e.g. some other n-sided polygonal hollow tube or pipe. The bottom of the sample holder 100 is sealed with a base 112, which may be of the same or a different material as that of the confining structure 110. The base 112 may be a separate piece, or form part of the confining structure 110.

The confining structure 110 has at least one region 120 which faces away from the axial direction A. Here, the region 120 is a rectangular shaped hole through the wall of the confining structure, and aligned approximately with a plane perpendicular to the axial direction A. It is, however, envisaged that such a region 120 may have different shapes, and that such a region 120 may not necessarily be a hole through e.g. a side wall of the confining structure 110 but a region with a finite but reduced thickness of such a wall.

The confining structure 110 as shown in FIG. 1a is preferably rigid, and made from a rigid material, i.e. with a Young's modulus of above or equal to 1.0, such as a rigid polymer material or a metal. It is, however, envisaged that the confining structure 110 may be at least partially flexible, and made from e.g. a flexible polymer material such as rubber. It is also envisaged that the confining structure 110 may be created from rigid parts that are joined together in a flexible way, such as by e.g. using hinges or similar functional elements, thereby creating a flexible structure. The confining structure 110 may, according to some embodiments, be formed of a plurality of different materials or structural elements. Such embodiments may for example include one or more helical bands forming the enclosure and providing support for the radiation transmitting regions 120, which hence may be formed of a material that differs from the material of the helical band(s). The helical bands may for example be wound in opposite directions so as to provide an improved torsional rigidity. Preferably, the band-shaped structure(s) may be wound with a pitch leaving a space between each turn, so that the space may be used as the radiation transmitting regions 120.

FIG. 1b illustrates the sample holder 100, wherein a sample in the form of a drill core sample 130 has been placed. The confining structure 110 encloses the sample 130 and restricts it from moving in a direction that intersects the axial direction A. During measurement, exciting radiation 140 coming from e.g. an X-ray source and which impinges on the sample may pass through the region 120 (which faces away from the axial direction A) of the confining structure 110 with no or little attenuation, emanate from the sample as transmitted radiation 144, and continue towards for example an X-ray transmission detector. Likewise, fluorescent radiation 142 which emanates from the sample 130 during measurement may also pass through the region 120 with no or little attenuation, and continue towards for example an X-ray fluorescence detector.

In some embodiments, the material of which the confining structure 110 is made has a majority of atoms having an atomic number of 9 or less. As an example, the material may be e.g. carbon or materials based on polymers such as for example polyethylene (PE), polypropylene (PP), polystyrene (PS) or acrylonitrile butadiene styrene (ABS). By using a majority of atoms having an atomic number of 9 or less, the interaction of the atoms with the X-ray radiation may be reduced.

FIG. 1c illustrates a sample holder 101 with a confining structure 111 in which a region 121 forms a hole through a wall of the confining structure 111. Like described earlier, the region 121 faces away from the axial direction A of the confining structure 111 and the sample holder 101, and allows X-ray radiation to impinge on and emanate from a sample 131 that is placed in the sample holder 101 and enclosed by the confining structure 111.

In some embodiments, axial direction A of the confining region 111 may align with a direction of gravity G during measurement. This may help to further fix the sample 131 in place and restrict it from moving in a direction intersecting that of the axial direction A, taking advantage of the weight of the sample 131 itself. This applies also when, as illustrated in FIG. 1c, the confining structure 111 has a width greater than that of the sample 131 as gravity and the weight of the sample 131 will keep the sample 131 fixed anyway.

Figure 2:
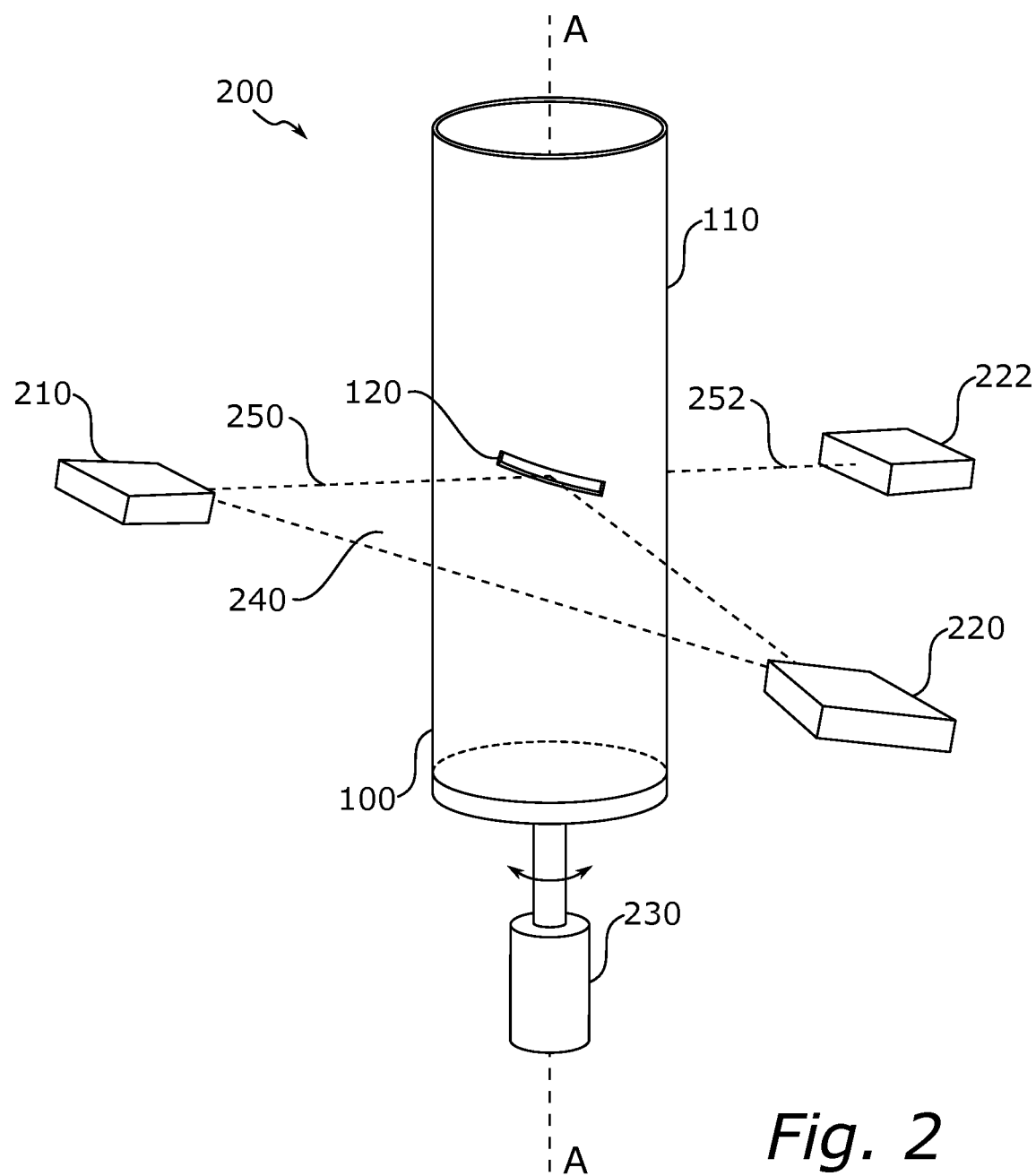
FIG. 2 illustrates an apparatus for measurement according to one or more embodiments of the present disclosure.

With reference to FIG. 2, an apparatus (or a system) for X-ray transmission measurement and X-ray fluorescence measurement of samples including drill core samples or drill cuttings will be described in more detail.

FIG. 2 illustrates an apparatus (or a system) 200 which includes a sample holder 100 as described herein, at least one X-ray source 210, at least one X-ray fluorescence detector 220 and at least one X-ray transmission detector 222. Although used for different purposes, it is envisaged that the detectors 220 and 222 may also be of a same type.

In addition, the apparatus 200 may comprise rotating means for rotating at least one of the sample holder 100, the X-ray source 210 and the X-ray detectors 220 and 222. Here, the rotating means includes a motor 230 which is arranged to rotate the sample holder 100 around the axial direction A. The motor may for example be a DC motor, a synchronous motor or e.g. a stepper motor. It is envisaged that rotating means may also be provided for rotating the X-ray source 210 and/or one or both of the X-ray detectors 220 and 222.

The X-ray source 210 may for example be an X-ray tube, a radioactive isotope, or any other suitable source. The X-ray source 210 may for example generate X-rays based on triboluminescence.

The X-ray detector 220 may for example be a scintillation detector, a semiconductor detector, a quantum dot detector or any other suitable detector.

If using radiation with other wavelengths (e.g. UV), a ray source may be e.g. a UV lamp, led or laser, and a detector may be e.g. a semiconductor UV photo diode or similar.

By using the rotating means, radiation from the X-ray source 210 may impinge on a sample at different locations during measurement, and fluorescent radiation emanating from the different locations of the sample may be received by the X-ray detector 220. Likewise, transmitted radiation emanating from the sample may be received by the X-ray detector 222. This may allow for a broader study of e.g. the concentration of chemical elements in the sample, as measurements at different locations of the sample may be obtained.

In some embodiments, the X-ray 210 or one or both of the X-ray detectors 220 and 222, or all, may be rotated around the sample. This may also allow for a broader study of the sample, as angular dependence of impinging and/or emanating radiation to/from the sample may be accounted for.

As illustrated in FIG. 2, the positions of the region 120, the X-ray source 210 and the X-ray detector 220 defines a plane 240. By aligning the region 120 such that its plane of extension aligns with the plane 240, the process of measuring may be improved. If, for example, the sample is being rotated by the rotating means 230, aligning the region 120 such that its plane of extension aligns with the plane 240 may allow for radiation to imping on or emanate from the sample through the region 120 during a larger time interval during measurement. As an example, consider that the region 120, the X-ray source 210 and the X-ray detector 220 are all positioned such that their positions define a plane which is perpendicular to the axial direction A. The region 120 may be formed as a rectangular hole through a wall of the confining structure 110, where the lengths of the longer and shorter sides of this rectangle are approximately one fourth and one twentieth, respectively, of the outer circumference of the cylindrical confining structure 110. If the region 120 is aligned such that its plane of extension (i.e. the longer rectangular sides) is aligned with the plane 240, radiation may impinge on and emanate from the sample through the region 120 for at least one fourth of a full rotation of the sample holder 110, allowing for a certain number of measurements to be performed during this time window. In contrast, if the region 120 is arranged such that its shorter sides aligns with the plane 240, the time window would instead correspond only to one twentieth of a full rotation of the sample, allowing for correspondingly fewer measurements to be performed.

If, for example, the region 120, the X-ray source 210 and the X-ray detector 220 are arranged such that the plane 240 intersects the axial direction at an angle different from approximately 90 degrees, it is envisaged to align the region 120 such that its plane of extension aligns with the plane 240 (that is, such that the region 120 is aligned such that it extends along a direction that forms a finite angle to a plane perpendicular to the axial direction A). By so doing, the time window described above may still be at least partially increased even if the sample holder 100 is rotated around an axis not perpendicular to the plane 240. As an example, if the plane 240 intersects the axial direction A at an angle of 45 degrees, aligning the region 120 such that it also extends along a direction that forms an angle of 45 degrees to a plane perpendicular to the axial direction may optimize the measurement process by the region at least momentarily being aligned with the plane 240 during rotation of the sample holder 100 around the axial direction A. If, for example, the plane 240 intersects the axial direction at an angle of 90 degrees (i.e. if the plane 240 is perpendicular to the axial direction A), the measurement process may be optimized by aligning the region 120 such that it is parallel to a plane perpendicular to the axial direction A and forms an angle of 0 degrees to the plane (i.e. such that the plane of the extension of the region is also perpendicular to the axial direction A).

Herein, the position of a region may preferably be defined as the center point of the region. It is, however, envisaged that other definitions may be used, such as the position of a corner of a region, an outer edge of a region or similar.

Impinging radiation 250 on a sample, from the X-ray source 210 and through the region 120, may be transmitted through the sample and emanate on the other side as transmitted radiation 252. Preferably, the X-ray detector 222 may be aligned such that the transmitted radiation 252 may be measured. The X-ray source 210 and the X-ray (transmission) detector 222 may be constructed such that they rotate along with each other, or the X-ray source 210 and the X-ray detector 222 may be aligned individually, using e.g. separate or joint means of rotation (such as e.g. motors).

With reference to FIGS. 3a, 3b, 3c, 3d and 3e, various examples of sample holders and regions in accordance with the present disclosure will be described in more detail.

Figure 3A:
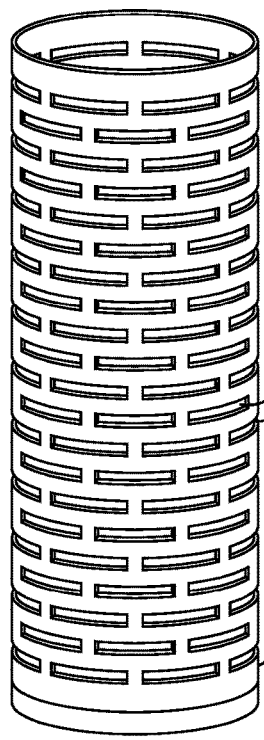
FIGS. 3a, 3b, 3c, 3d and 3e illustrate examples of sample holders and regions according to one or more embodiments of the present disclosure.

FIG. 3a illustrates a sample holder 300, including a confining structure 310 that may enclose a sample placed in the sample holder 300, and a plurality of regions 320. The regions 320 all face away from the axial direction A of the confining region 310, and allow exciting radiation impinging on the sample (e.g. from an X-ray source) and fluorescent radiation emanating from the sample during measurement to pass therethrough. The principle of the regions 320 are equivalent to the one or more regions already described herein, but by adding more than one region 320 the measurement process may be further optimized. For example, if the sample holder 300 is rotated during measurement, multiple regions 320 may help extend the combined time window during which measurements may be taken through one of the regions 320.

In FIG. 3a, the regions 320 are formed as rectangular holes through the confining structure 310, where the regions 320 are aligned such that the plane of their extension is parallel with a plane perpendicular to the axial direction of the confining structure 310. It is, as mentioned earlier, envisaged that the form of such holes (or regions) may be different from rectangular, such as e.g. squares, circles, ovals, n-sided polygons or similar, and that they may be arranged at different angles. The regions 320 are arranged in an ordered pattern such that their center points fall on a rectangular lattice. It is, however, envisaged that the regions 320 may also be arranged such that their center points fall on a different ordered lattice, such as a rhombic, hexagonal, rectangular, square or parallelogrammic lattice, or in an ordered but not periodic quasicrystalline pattern.

Figure 3B:
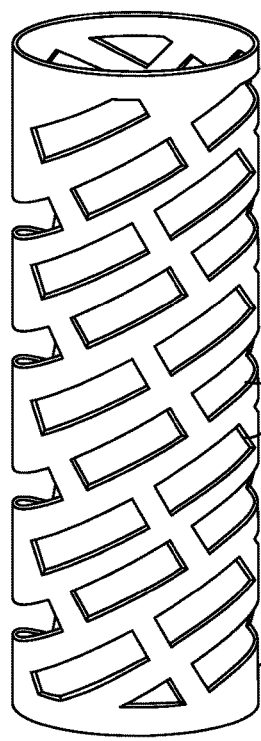

FIG. 3b illustrates a sample holder 301, including a confining structure 311 that may enclose a sample placed in the sample holder 301, and a plurality of regions 321. Like the regions 320 in FIG. 3a, the regions 321 in FIG. 3b are arranged in an ordered pattern corresponding to a rectangular lattice, but here they are aligned such that they extend along a direction that forms an angle to a plane perpendicular to an axial direction of the confining structure 311. The angle is here approximately 40 degrees, but it is envisaged that other angles, such as between more than 0 and up to and including 90 degrees may also be used.

Figure 3C:
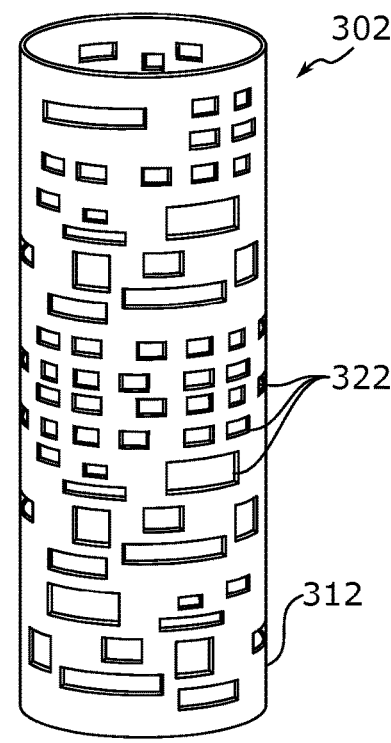

FIG. 3c illustrates a sample holder 302, including a confining structure 312 that may enclose a sample placed in the sample holder 302, and a plurality of regions 322. Here, the regions 322 are still rectangular in shape but arranged in a random pattern, such that the center points of the regions 322 do not fall on any particular ordered pattern such as in FIGS. 3a and 3b. The regions 322 have different ratios between the lengths of their longer sides and their shorter sides, and the regions 322 have different sizes in terms of area. The regions 322, arranged in the random pattern and with different sizes and forms, may be advantageous if e.g. a statistical property of the sample is to be measured. By e.g. the random pattern, bias effects due to e.g. an ordered arrangement of the regions may be avoided. It is also envisaged that all regions 322 may have the same size but still be arranged in a random pattern. Likewise, it is also envisaged that the regions 322 have varying sizes but are placed in an ordered pattern. In general, the arrangement and/or size and shape of regions 322 may be optimized in accordance with what property of the sample that is to be measured.

In general, it is envisaged that not all regions belonging to a confining structure may be of equal size and/or shape. It may be envisaged that for example some regions in a plurality of regions are square, while others are oval or circular, and/or that some regions in a plurality of regions are smaller than other regions.

Figure 3D:
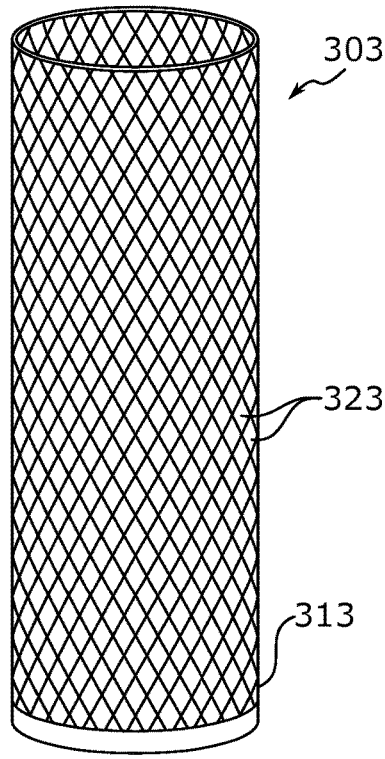

FIG. 3d illustrates a sample holder 303, including a confining structure 313 formed like a wire mesh, and where the regions 323 cover a vast majority of the surface of the confining structure 313. In this arrangement, the confining structure 313 may be formed from e.g. a metal. As the regions 313 cover a larger area of the confining structure 313, the material properties of the confining structure 313, such as the atomic numbers of the atoms included in the material, may be less significant and have less impact on the attenuation of radiation.

In order to allow measurement not only on drill core samples but also on drill cuttings, it is envisaged that the confining structure 313 may be complemented by a thin layer of e.g. paper or plastic in order to prevent a sample, or pieces of a sample, to escape through the regions 323. Such a layer may form part of the confining structure 313 itself, or be added as a separate entity.

Figure 3E:
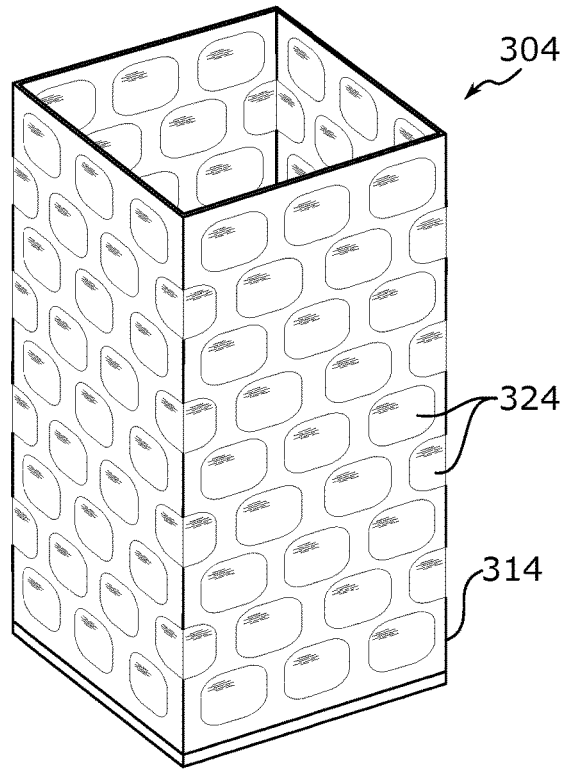

FIG. 3e illustrates a sample holder 304, including a confining structure 314 which is formed as a hollow rectangular pipe. The confining structure 314 includes a plurality of regions 324. Here, the regions 324 are not holes in the walls of the confining region 324, but areas that has a reduced but finite thickness. For example, the confining structure 314 may have a thickness of a couple of millimeter between the regions 324, while the regions 324 themselves may have a thickness of e.g. one millimeter or less. By using regions 324 with reduced but finite thickness instead of holes, the sample holder 304 may hold also samples in form of small drill cuttings or even powder, while still allowing for radiation to pass through the regions 324 with no or little attenuation or interaction. In other embodiments, it may be envisaged that the regions 324 have the same thickness as the rest of the confining structure 314, but that instead the regions 324 are created from a material having a lower or no attenuation of rays (such as X-rays) passing therethrough.

A sample holder as defined herein is preferably formed such that it may hold a drill core sample having a diameter of approximately 20 to 100 mm. The confining structure of a sample holder preferably has an inner dimension (i.e. a diameter, width or effective diameter) which slightly exceeds the outer dimension of a drill core sample. However, as have been illustrated herein, a sample holder may also have a larger inner dimension and still properly fix e.g. a drill core sample. Regarding the length of a sample holder as defined herein, the length (e.g. of the confining structure) is preferably in the interval between 10 to 300 cm, although it is envisaged that a sample holder may have lengths that are either shorter or greater than that.

By using a sample holder in accordance with the present disclosure, the sample may be fixed within the sample holder during measurement and prevent from moving. At the same time, a sample holder in accordance with the present disclosure may allow radiation to reach and leave the sample during measurement with low enough attenuation to still maintain exciting and detectable properties, respectively. A sample holder, and an apparatus, in accordance with the present disclosure may therefore offer an improved way of performing X-ray measurements, such as X-ray transmission and X-ray fluorescent measurements, on drill core samples and/or drill cuttings.

The person skilled in the art realizes that the present disclosure is by no means limited to the embodiments described above. On the contrary, many modifications and variations are possible within the scope of the appended claims.

Although features and elements are described above in particular combinations, each feature or element may be used alone without the other features and elements or in various combinations with or without other features and elements.

Additionally, variations to the disclosed embodiments can be understood and effected by the skilled person in practicing the claimed invention, from a study of the drawings, the disclosure, and the appended claims. In the claims, the word "comprising" does not exclude other elements, and the indefinite article "a" or "an" does not exclude a plurality. The mere fact that certain features are recited in mutually different dependent claims does not indicate that a combination of these features cannot be used to advantage.

The invention claimed is:

1. A sample holder for holding a sample comprising a drill core sample during X-ray transmission measurements and fluorescence measurements, the drill core sample having a diameter and length comprising
 a confining structure having a length direction and a lateral surface, and being sized and shaped to receive a drill core sample, the confining structure adapted to, during measurement, at least partially enclose the drill core sample and to restrict movement of the drill core sample in a direction intersecting the length direction, said confining structure comprising a plurality of holes through the confining structure facing away from the length direction and allowing exciting radiation impinging on, and fluorescent radiation emanating from, the drill core sample during measurement to pass therethrough, said plurality of holes being arranged on the lateral surface and being separated from each other in at least one of the length direction and a direction perpendicular to the length direction to allow exciting radiation impinging on, and fluorescent radiation emanating from, the sample during measurement to pass therethrough.

2. The sample holder according to claim 1, wherein the confining structure is rigid.

3. The sample holder according to claim 1, wherein the confining structure comprises a shape conforming to a hollow cylinder to receive the drill core sample.

4. The sample holder according to claim 1, wherein at least part of the confining structure is formed from a polymer material.

5. The sample holder of claim 4, said polymer material having a majority of atoms with atomic number 9 or less.

6. The sample holder according to claim 1, adapted such that, during measurement, the length direction aligns with a direction of gravity.

7. The sample holder according to claim 1, wherein the regions in the plurality of regions are arranged in an ordered pattern.

8. The sample holder according to claim 1, wherein the at least one region extends along a direction forming an angle to a plane perpendicular to the length direction.

9. The sample holder according to claim 8, wherein the angle is between 0 to 90.

10. An apparatus for X-ray transmission measurement and fluorescence measurement of drill core samples having a diameter and a length, said apparatus being adapted for receiving a drill core sample holder according to claim 1, and comprising an X-ray source, an X-ray transmission detector, a fluorescence detector and rotating means for rotating at least one of the sample holder, the X-ray source, the X-ray transmission detector and the fluorescence detector.

11. The apparatus according to claim 10, further configured such that during rotation of at least one of the drill core sample holder, the ray source and the fluorescence detector, a plane of an extension of the at least one region of the drill core sample holder at least momentarily aligns with a plane defined by the positions of the ray source, the fluorescence detector and the at least one region of the drill core sample holder.

12. The apparatus according to claim 11, further configured such that the extension of the plane of the at least one region aligns with the plane for at least one full rotation of at least one of the drill core sample holder, the ray source and the fluorescence detector.

13. The apparatus according to claim 10, wherein the ray source is an X-ray source, and wherein at least one of the fluorescence detector is an X-ray detector.

14. A system for X-ray transmission measurement and fluorescence measurement of samples comprising drill core samples, comprising an apparatus according to claim 10.

15. A system for X-ray transmission measurement and fluorescence measurement of samples comprising drill core samples, comprising a sample holder according to claim 1.

* * * * *